(12) United States Patent
Schwaiger et al.

(10) Patent No.: US 11,666,723 B2
(45) Date of Patent: Jun. 6, 2023

(54) NASAL CANNULA HAVING IMPROVED AND ASYMMETRICAL FLOW CONTROL

(71) Applicant: Hamilton Medical AG, Bonaduz (CH)

(72) Inventors: Ingo Schwaiger, Chur (CH); Sandro Walker, Chur (CH)

(73) Assignee: HAMILTON MEDICAL AG, Bonaduz (CH)

( * ) Notice: Subject to any disclaimer, the term of this patent is extended or adjusted under 35 U.S.C. 154(b) by 333 days.

(21) Appl. No.: 17/273,495

(22) PCT Filed: Sep. 10, 2019

(86) PCT No.: PCT/EP2019/074124
§ 371 (c)(1),
(2) Date: Mar. 4, 2021

(87) PCT Pub. No.: WO2020/053220
PCT Pub. Date: Mar. 19, 2020

(65) Prior Publication Data
US 2021/0338960 A1 Nov. 4, 2021

(30) Foreign Application Priority Data

Sep. 14, 2018 (DE) ...................... 10 2018 122 516.4

(51) Int. Cl.
*A61M 16/06* (2006.01)
(52) U.S. Cl.
CPC ..... *A61M 16/0672* (2014.02); *A61M 2206/20* (2013.01)
(58) Field of Classification Search
CPC ....................................... A61M 16/0666–0677
See application file for complete search history.

(56) References Cited

U.S. PATENT DOCUMENTS

| 3,754,552 | A | 8/1973 | King | |
|---|---|---|---|---|
| 2005/0241644 | A1* | 11/2005 | Gunaratnam | A61M 16/0825 128/207.18 |

(Continued)

FOREIGN PATENT DOCUMENTS

| DE | 202014100110 | 1/2014 |
|---|---|---|
| WO | 2004073778 | 9/2004 |
| WO | 2014142681 | 9/2014 |

OTHER PUBLICATIONS

International Preliminary Report on Patentability dated Mar. 9, 2021.

(Continued)

*Primary Examiner* — Rachel T Sippel
(74) *Attorney, Agent, or Firm* — Rankin, Hill & Clark LLP (57) ABSTRACT

A nasal cannula includes a distribution conduit running along a virtual distribution path. The distribution path defines a longitudinal direction and has two branch openings. A respective supply conduit branches off from each branch opening. The distribution conduit also has two coupling openings arranged spaced apart from the branch openings. The nasal cannula has a plug via which one of the two coupling openings can be sealed as a closure opening. Another of the two coupling openings is designed as a supply opening. The plug has a flow-directing configuration with an exposed flow-directing surface. In a reference state in which the plug is closing the closure opening, the flow-directing surface is arranged in the distribution conduit in the longitudinal extension region of at least one branch opening and positioned relative to the distribution path to deflect treatment gas flowing in the distribution conduit from the supply opening along the distribution path towards at least one of the branch openings.

18 Claims, 5 Drawing Sheets

(56) References Cited

U.S. PATENT DOCUMENTS

| | | | |
|---|---|---|---|
| 2011/0067704 A1* | 3/2011 | Kooij | A61M 16/0858 |
| | | | 128/207.18 |
| 2014/0158127 A1 | 6/2014 | Boucher | |
| 2016/0271353 A1 | 9/2016 | Cheung | |

OTHER PUBLICATIONS

International Search Report filed in PCT/EP2019/074124 dated Dec. 5, 2019.
German Search Report filed DE 10 2018 122 516.4 dated Jul. 31, 2019.

* cited by examiner

NASAL CANNULA HAVING IMPROVED AND ASYMMETRICAL FLOW CONTROL

The present application relates to a nasal cannula for nasally supplying a patient with therapeutic gas, encompassing a distribution conduit component having a distribution conduit that extends along a virtual distribution path passing centrally through it; the distribution path defining a longitudinal direction; the distribution conduit comprising two branch openings; a respective supply conduit for supplying the patient with therapeutic gas from the distribution conduit branching off from each branch opening; the distribution conduit comprising, in addition to the branch openings, two coupling openings arranged at a distance from the branch openings; the nasal cannula encompassing a plug with which one of the two coupling openings, constituting a closure opening, is closable by the plug for a flow of gas through it; and a further one of the two coupling openings, constituting a delivery opening, being embodied for connection of a gas delivery line to the distribution conduit.

A nasal cannula of this kind is known from U.S. Pat. No. 3,754,552 A. The great advantage of this known nasal cannula is that each of the two coupling openings can be a delivery opening and a closure opening, depending on which of the two coupling openings the plug is introduced into, and depending on which other of the two coupling openings has a gas delivery line connected to it. The known nasal cannula thus allows therapeutic gas to be conveyed to a patient on the right or the left side of his or her body, depending on which of the two sides is more advantageous for the conveyance of therapeutic gas as a function of the respective patient situation. The plug serves to close off the coupling opening that is not required for gas delivery, in order to avoid undesired emergence of therapeutic gas from the distribution conduit, which gas would then not flow out of the branch openings and thus would not reach the patient.

In order to allow the coupling openings on the known distribution conduit component to be embodied sufficiently reliably for attachment of the plug and of a gas delivery line, the distribution conduit component extends a comparatively long distance along the distribution path on both sides of the branch openings. A disadvantage of the known nasal cannula is that in the region between the coupling opening used by the plug and constituting a closure opening, and the branch openings, a comparatively large dead space is formed in which therapeutic gas flows and eddies in uncontrolled fashion as a patient is being supplied; this results in disadvantageously unpredictable gas emergence conditions at the branch openings.

The object of the present Application is therefore to improve the nasal cannula recited initially in such a way that despite the use of a plug in a coupling opening used as a closure opening, the flow conditions in the distribution conduit are more defined than hitherto, and thus on the one hand fewer flow losses occur in the distribution conduit, and on the other hand a more defined outflow of therapeutic gas through the branch openings to the patient occurs.

The present invention achieves this object by way of a nasal cannula of the kind recited initially in which the plug comprises a flow-directing configuration having an exposed flow-directing surface; the flow-directing surface being arranged, in a reference state in which the plug is arranged on the nasal cannula so as to close off the closure opening as intended, in the distribution conduit in the longitudinal region of extent of at least one branch opening, and being canted with respect to the distribution path in such a way that it deflects therapeutic gas, flowing in the distribution conduit in from the delivery opening along the distribution path, to at least one of the branch openings.

Unless stated otherwise in a specific instance in the present Application, the nasal cannula of the present Application is described in the reference state characterized above.

The exposed flow-directing surface of the flow-directing configuration, which in the reference state faces toward the therapeutic gas flowing in from the delivery opening and is wettable thereby, can deflect the therapeutic gas flowing in from the delivery opening in as loss-free a manner as possible to the branch opening in whose longitudinal region of extent the flow-directing surface is arranged. In order to perform this deflection function, the flow-directing surface is canted relative to the distribution path, i.e. the distribution path encloses an angle with the flow-directing surface. In the simplest case, the flow-directing surface can be a flat or at least locally flat surface. For particularly loss-free deflection of the therapeutic-gas flow, however, the flow-directing surface is preferably an at least locally curved surface. The flow-directing surface can be embodied to be curved along its entire longitudinal extent along the distribution path.

As a rule, a deflection through approximately 90°, i.e. approximately a right angle, of the therapeutic-gas flow initially proceeding along the distribution path to the branch opening is desirable. For this, it is advantageous in terms of deflection in as loss-free a manner as possible if the flow-directing surface has a concave curvature. A flow-directing surface that is curved as continuously as possible is advantageous for maximally loss-free deflection of the therapeutic-gas flow in the distribution conduit component, and for that reason the flow-directing surface can preferably have a concave curvature over its entire length of extent. In order to achieve the 90° deflection from the distribution path to the branch opening, the flow-directing surface is preferably concavely curved at least locally around a curvature axis orthogonal to the distribution path.

The flow-directing surface can comprise differently curved portions in order to furnish maximally uniform therapeutic-gas flow volumes at both branch openings. Because the branch openings as a rule are at different distances from the flow-directing surface, achieving quantitatively identical flow volumes in both branch openings is difficult, but according to a preferred refinement it is attainable, for instance, by the fact that the flow-directing surface comprises along the distribution path two concavely curved portions that comprise between them a convexly curved portion.

Preferably the flow-directing surface comprises only those portions and is made up thereof. A flow-directing surface curved in these multiple different ways is preferably curved in each portion around a curvature axis orthogonal to the distribution path. The flow-directing surface is preferably uncurved in a width direction of the distribution conduit, i.e. orthogonally to the distribution path.

Even when the flow-directing surface is curved around the aforesaid curvature axis orthogonal to the distribution path, eddies can form in the regions of the distribution conduit close to the walls if the flow-directing surface opens into the wall of the distribution conduit, for example, at an angle, forming a corner. In order to avoid such undesired eddying, according to a preferred refinement of the present invention provision is made that the flow-directing surface, concavely curved around a curvature axis orthogonal to the distribution path, is also curved around a curvature axis extending along the distribution path. This flow-directing surface preferably comprises only concavely curved surface regions, but no convexly curved surface regions.

In principle, the therapeutic gas can flow out of the branch openings, directly after passing through them, as a free flow from the distribution conduit component to the patient who is wearing the nasal cannula. Usually, however, the distribution conduit is worn at a certain distance from the nostrils. For controlled delivery of therapeutic gas, the nasal cannula comprises the supply conduits which proceed from the branch openings and project from the distribution conduit component. During therapy, these supply conduits extend to a patient's nostrils or in fact extend some distance through the nostrils into the nasal cavities. A respective supply conduit proceeds from each branch opening. The supply conduits can be embodied identically, or mirror-symmetrically with respect to an axis of symmetry orthogonally intersecting the distribution path between the branch openings.

The flow-directing surface extends at least in the longitudinal region of extent, i.e. in the region of extent along the distribution path, of the branch opening located closer to the respective closure opening. It is thereby possible to ensure that the flow-directing surface can effectively and controllably deflect a therapeutic-gas flow at least to that branch opening which is located closer to the closure opening. It is not to be excluded, however, that the flow-directing surface also extends into the longitudinal region of extent of the branch opening located farther from the respective closure opening, or in fact extends completely beyond it. In this case the deflection of the therapeutic-gas flow flowing in from the delivery opening along the distribution path is achieved over a long region of the distribution conduit, in low-impact fashion and with little loss.

The at least locally concave and/or convex curvature of the flow-directing surface around a respective curvature axis orthogonal to the distribution path can change quantitatively along its course. Preferably the concave curvature of a concavely curved portion of the flow-directing surface around a curvature axis orthogonal to the distribution path increases with increasing proximity to the associated branch opening, i.e. the radius of curvature extending from the aforesaid curvature axis becomes shorter with increasing proximity of the flow-directing surface to the branch opening associated with the flow-directing surface.

In order to introduce therapeutic gas into the distribution conduit of the distribution conduit component, the nasal cannula preferably comprises a connector fitting that is introducible into the delivery opening for connection of a gas delivery line. To avoid eddy-forming discontinuities in the distribution conduit or along a wall that guides the therapeutic-gas flow in the distribution conduit component, according to a preferred refinement of the present invention an inner surface of the connector fitting which directs a gas flow through the connector fitting, when arranged as intended in operationally ready fashion on the nasal cannula, forms a continuous flow-conveying surface with the flow-directing surface of the plug. An unavoidable join occurs at the abutment point of the inner surface of the connector fitting and the flow-directing surface, but no eddies occur there if the inner surface and the flow-directing surface form a common flow-conveying surface that is flush across the join. The common continuous flow-conveying surface is preferably devoid of discontinuities and inflections at the aforesaid join.

In order to facilitate correct arrangement of the plug and connector fitting relative to one another, according to a refinement of the present invention provision can be made that the plug comprises a positive-engagement configuration and that the connector fitting comprises a counterpart positive-engagement configuration, the positive-engagement configuration and the counterpart positive-engagement configuration being in positive engagement with one another in the operationally ready state. The plug and the connector fitting can have a conical/circularly conical or circularly cylindrical outer wall on their outer side that is radially external with respect to the distribution path in the operationally ready state, but can have on their radially internal inner surface a wall that radially externally delimits the flow and does not have a circular cross section. When the aforementioned continuous flow-conveying surface is to be constituted jointly by the flow-directing surface and the inner surface of the connector fitting, correct relative arrangement of the plug and connector fitting with respect to one another is particularly important. This correct relative arrangement can be reliably achieved by way of the aforesaid configurations (positive-engagement configuration and counterpart positive-engagement configuration). To ensure that misalignment of the connector fitting and plug relative to one another in the operationally ready state is precluded, the positive-engagement configuration and the counterpart positive-engagement configuration are preferably in positive engagement with one another only in the operationally ready state.

The positive-engagement configuration and the counterpart positive-engagement configuration are preferably embodied according to the lock-and-key principle. For this purpose, one of the configurations from among the positive-engagement configuration and counterpart positive-engagement configuration can comprise a projection, and the respective other configuration can comprise a recess into which the projection can be introduced only when the connector fitting and the plug are correctly oriented relative to one another, in particular are correctly oriented relative to one another in terms of their angular orientation around the distribution path.

Twist prevention for the connector fitting and the plug relative to one another is achieved by way of the positive-engagement configuration and the counterpart positive-engagement configuration. When a positive engagement has been established, a relative rotation of the plug and connector fitting relative to one another is prevented.

Because the positive engagement is established as a rule in the distribution conduit component, and specifically at a location in the distribution conduit component which is not visible to a caregiver or to the physician performing therapy, one or both configurations can comprise an introduction aid for establishing the positive engagement. One configuration, from among the positive-engagement configuration and counterpart positive-engagement configuration, which comprises a projection can thus be tapered toward the freely protruding end. Additionally or alternatively, a recess, which constitutes the respective other configuration from among the positive-engagement configuration and counterpart positive-engagement configuration and receives the projection, can be embodied to taper from the longitudinal introduction end in an introduction direction of the projection.

Not only the relative arrangement of the plug and connector fitting, but also a correct location of the connector fitting relative to the distribution conduit component, are advantageous for correct functioning of the nasal cannula discussed here. A correct location of the connector fitting relative to the distribution conduit component can be achieved by the fact that the connector fitting comprises an arrangement configuration; and that the distribution conduit component comprises a counterpart arrangement configuration in the region of the delivery opening, the arrangement configuration and the counterpart arrangement configuration being in positive engagement with one another in the operationally ready state. This positive engagement prevents a displacement of the connector fitting and distribution conduit component relative to one another, in particular around the distribution path, out of the correct relative arrangement that has been established.

It is preferred in turn, in order to preclude misalignment of the connector fitting and distribution conduit component, that the above-described positive engagement between the arrangement configuration and counterpart arrangement configuration exist only when the nasal cannula is in the operationally ready state, or be establishable only in the context of an installation of the nasal cannula which results in the operationally ready state. The statements made above with regard to the positive-engagement configuration and counterpart positive-engagement configuration apply correspondingly to the possible conformations of the arrangement configuration and the counterpart arrangement configuration, with the stipulation that the statements made regarding the positive-engagement configuration apply to the arrangement configuration, and that the statements made regarding the counterpart positive-engagement configuration apply to the counterpart arrangement configuration. One configuration from among the arrangement configuration and counterpart arrangement configuration can therefore comprise a projection, and the respective other configuration can comprise a recess.

Because the distribution conduit component as a rule radially externally surrounds the connector fitting and/or is embodied with comparatively thin walls, the distribution conduit component preferably comprises the projection, and the connector fitting comprises the recess. While one configuration from among the positive-engagement configuration and counterpart positive-engagement configuration is preferably a projection that protrudes parallel to the distribution path from the structure carrying it, the projection of one configuration from among the arrangement configuration and counterpart arrangement configuration is preferably a radial projection that protrudes toward the distribution path or (also possibly) protrudes away from the distribution path from a component that carries it. The recess of the respective other configuration is accordingly also a radial recess. The projection, constituting a radial projection, can be embodied as an introduction aid along the distribution path with decreasing radial height and/or with a decreasing projection width to be measured in a circumferential direction around the distribution path.

For correct arrangement of the plug as well relative to the distribution conduit component, the plug can comprise an orientation configuration. The distribution conduit component can likewise comprise a counterpart orientation configuration in the region of the closure opening, the orientation configuration and the counterpart orientation configuration being in positive engagement with one another in the operationally ready state, preferably (for the reasons already recited) only in the operationally ready state.

Because both the plug and the connector fitting as a rule are introduced into (or, in the case of the connector fitting, also placed onto) the distribution conduit component axially, i.e. along the distribution path, because of the shared arrangement motion of the plug and connector fitting relative to the distribution conduit component, the statements made for the arrangement configuration and counterpart arrangement configuration also apply to the orientation configuration and counterpart orientation configuration, with the stipulation that the statements made for the arrangement configuration are relevant to the orientation configuration, and the statements made for the counterpart arrangement configuration are relevant to the counterpart orientation configuration. This includes the fact that the statements made for the positive-engagement configuration are also relevant to the orientation configuration, and the statements made for the counterpart positive-engagement configuration are relevant to the counterpart orientation configuration. One of the two configurations can be a projection, and the respective other configuration can be a recess receiving the projection in positive engagement. It is thereby possible to establish twist prevention for the plug relative to the distribution conduit component, as well as twist prevention for the connector fitting to prevent twisting around the distribution path relative to the distribution conduit component.

In order to allow a patient using the nasal cannula to be supplied with therapeutic gas selectably from each of the two sides of his or her body depending on the therapeutic situation, according to a refinement of the present invention the two coupling openings are embodied similarly at least to the extent that each of the two coupling openings can be both a closure opening and a delivery opening. At least those longitudinal end regions of the distribution conduit which comprise the coupling openings can be embodied mirror-symmetrically.

To prevent an arrangement of the plugs and/or connector fitting in either of the coupling openings from resulting in different flow conditions in the distribution conduit, the plug and/or the connector fitting are preferably embodied mirror-symmetrically with regard to a symmetry plane containing their respective longitudinal axis. In the reference state, the distribution path lies in the symmetry plane of the plug, at least in the region in which the flow-directing surface is arranged. It is correspondingly the case for the connector fitting that the distribution path is located in the symmetry plane at least at the gas outlet end of the connector fitting.

An asymmetrical delivery of therapeutic gas to the patient is desired in some therapeutic instances. Because therapeutic gas is introduced into the distribution conduit component via the gas inlet at only one point (the delivery opening), an asymmetrical distribution of therapeutic gas must be brought about inside the distribution conduit component and/or in the supply conduits (if present).

Measures are already known in the existing art for discharging therapeutic gas from a nasal cannula asymmetrically, i.e. in unequal quantities per unit time, to the individual nostrils of a patient. It is known, for example, to use supply conduits having different lengths and/or different flow cross sections. These measures taken at the supply conduits for nonuniform quantitative distribution of therapeutic gas to the two nostrils of a patent have the disadvantage, however, that they interact physiologically with the patient. The patient will possibly detect the longer of two supply conduits of unequal length, and/or the supply conduit having the larger opening cross section, in his or her nasal cavities. This can be unpleasant during therapy, and can jeopardize therapeutic success.

The present invention, conversely, furnishes the capability of delivering therapeutic gas to a patient, or causing it to flow through the branch openings, in unequal quantities per unit time, without requiring non-identically or asymmetrically configured supply conduits for that purpose. A nasal cannula having preferably mirror-symmetrically arranged supply conduits can therefore also be used to administer therapeutic-gas flow volumes of unequal magnitudes. The supply-conduit symmetry plane of the symmetrically embodied supply conduits is a plane that orthogonally intersects the distribution conduit path at half the distance between the branch openings.

According to a particularly preferred refinement of the present invention, administration in this fashion of different therapeutic-gas flow volumes through the two branch openings can be achieved by the fact that the plug, in the state arranged in the closure opening, at least partly closes off the branch opening located closer to the closure opening.

The branch openings are preferably of identical size or are mirror-symmetrical with respect to the aforesaid supply-conduit mirror-symmetry plane, but are embodied preferably with the same opening cross section, not only so that in principle administration of therapeutic-gas flow volumes of quantitatively equal size through the two branch openings is possible, but also so that a transposition of the closure opening and delivery opening results in quantitatively identical therapeutic-gas flow volumes through the branch openings but at the respective other branch opening compared with before the transposition.

This embodiment of a nasal cannula with an inner flow-directing surface in a distribution conduit, which deflects the therapeutic gas flowing in from the delivery opening to a branch opening and in that context brings about intentionally quantitatively different therapeutic-gas flow volumes through the two branch openings, is sufficiently preferred that the Applicant reserves the right to seek patent protection for a nasal cannula for nasally supplying a patient with therapeutic gas, encompassing a distribution conduit component having a distribution conduit that extends along a virtual distribution path passing centrally through it; the distribution path defining a longitudinal direction; the distribution conduit comprising two branch openings; a respective supply conduit for supplying the patient with therapeutic gas from the distribution conduit branching off from each branch opening; the distribution conduit comprising, in addition to the branch openings, a delivery opening that is arranged at a distance from the branch openings and is embodied for connection of a gas delivery line to the distribution conduit; the nasal cannula comprising a flow-directing configuration having a flow-directing surface exposed in the distribution conduit; the flow-directing surface being arranged in the distribution conduit in the longitudinal region of extent of at least one branch opening and being canted with respect to the distribution path in such a way that it deflects therapeutic gas, flowing in the distribution conduit from the delivery opening along the distribution path, to at least one of the branch openings; the branch opening to which the flow-directing surface extends along the distribution path having a smaller opening cross-sectional area than the respective other branch opening.

A nasal cannula of this kind can comprise two nasal-cannula halves that are produced movably relative to one another and can be assembled to yield the nasal cannula. This nasal cannula, which in contrast to the one recited previously does not comprise a plug and in which the flow-directing surface is provided nondisplaceably as a delimiting wall of the distribution conduit, achieves the same effect as the nasal cannula having a branch opening partly closed off by the plug: one of the two branch openings has a smaller opening cross-sectional area, so that a smaller quantity of therapeutic gas emerges per unit time through the branch opening having a smaller opening cross-sectional area (i.e., in the case of the nasal cannula having a plug, the partly closed-off branch opening) than through the other branch opening having a larger opening cross-sectional area.

In a refinement of the present invention, in order to assist a deflection of therapeutic gas flowing in from the delivery opening to the two branch openings, the aforementioned flow-directing configuration can be a first flow-directing configuration that deflects therapeutic gas, flowing in from the delivery opening along the distribution path, to one of the branch openings, the plug having a second flow-directing configuration having a second flow-directing surface that is arranged at a distance along the distribution path from the first flow-directing configuration and that, in the reference state, deflects therapeutic gas, flowing in from the delivery opening along the distribution path, to the respective other branch opening.

The first and the second flow-directing surface preferably do not constitute a continuous directing surface, so that preferably they are not portions of one and the same directing surface.

The statements made above regarding the physical embodiment of the first flow-directing configuration having the first flow-directing surface also apply to the second flow-directing configuration having the second flow-directing surface. In particular, the second flow-directing surface, like the first flow-directing surface, can be concavely curved around at least one of the aforementioned curvature axes in order to deflect to its branch opening the therapeutic gas that is flowing along the distribution path. The second flow-directing surface is preferably quantitatively smaller than the first flow-directing surface, and preferably the second flow-directing surface is concavely curved only around one or around two mutually orthogonal curvature axes. This prevents undesired noise generation in the distribution conduit during therapeutic operation.

The second flow-directing configuration, which is arranged upstream from the first flow-directing configuration in terms of a flow of therapeutic gas flowing in from the delivery opening along the distribution path, represents a flow obstacle for the flow of therapeutic gas to the first flow-directing configuration. In a more specific physical embodiment, the second flow-directing configuration can therefore extend over only a sub-portion of the distribution conduit and, in its region of extent, can deflect a gas flow flowing in along the distribution path into the respective other branch opening, and in the reference state can constitute outside its region of extent, with the distribution conduit, a flowthrough opening for a flow of therapeutic gas past the second flow-directing configuration to the first flow-directing surface. A portion of the therapeutic gas flowing in from the delivery opening can flow through this flowthrough opening to the first flow-directing configuration.

In order to bring about maximally effective deflection by the second flow-directing surface of a therapeutic-gas flow portion into the respective other branch opening, it is advantageous if the second flow-directing configuration abuts against an inner wall of the distribution conduit over a predetermined angular region around the distribution path. No gap then exists, at least in the angular region, between the second flow-directing configuration, in particular the second flow-directing surface, and the inner wall of the distribution conduit. Such a gap is undesired, since therapeutic gas can flow through it instead of being deflected by the second flow-directing surface into the respective other branch opening. The angular region can be constituted from several angular sub-regions located at a distance from one another, for instance if the angular region extends over the respective other branch opening where, because of the respective other branch opening, no inner wall of the distribution conduit is located. The second flow-directing configuration can thus also at least partly cover the respective other branch opening associated with it, so as to quantitatively influence, in the context of a predefined therapeutic-gas flow in the distribution conduit, the therapeutic-gas flow volume flowing through the respective other branch opening.

If quantitatively differing therapeutic-gas flow volumes through the two branch openings and/or out of the supply conduits are desired, this can also be achieved, alternatively or in addition to the feature already recited above of a partial covering of one branch opening, by the fact that a cross-sectional area, flowthrough-capable for therapeutic gas, of the flowthrough opening is larger or smaller than half the cross-sectional area of the distribution conduit at the location of the flowthrough opening.

The flowthrough opening is preferably either larger than 70% of the cross-sectional area of the distribution conduit at the location of the flowthrough opening, or smaller than 30% of the cross-sectional area of the distribution conduit, in order to generate therapeutic-gas flow volumes through the two branch openings which clearly differ from one another in terms of quantity.

The embodiment of a second flow-directing configuration, as recited above, can also be implemented on the aforementioned plug-free nasal cannula, for instance if it is produced from two nasal-cannula components using the injection-molding method.

The plug-containing nasal cannula recited initially can be brought into an operationally ready state in particularly simple fashion if the distribution conduit component is constituted from a material that has a lower modulus of elasticity than the material of the plug and/or of the connector fitting, so that the distribution conduit component is deformable by the respective insertion component upon introduction of one insertion component from among the plug and/or connector fitting into the distribution conduit component.

According to a preferred refinement of the present invention, for maximally simple connectability of the connector fitting to the coupling opening that is then used as a delivery opening, the two coupling openings are located at opposite longitudinal ends of the distribution conduit. The distribution path preferably extends in a straight line between the two coupling openings in order to avoid undesired deflection losses and noise generation. Additionally or alternatively, the two branch openings are located centeredly in a longitudinal direction between the coupling openings so that assuming otherwise identical operating conditions, the same flow conditions (but laterally reversed) occur in the distribution conduit regardless of which coupling opening is selected as a delivery opening.

The present invention furthermore relates to a nasal cannula therapy kit encompassing a nasal cannula as described above, and at least two or preferably more than two plugs that differ in terms of the length of the first and/or of the second flow-directing configuration, and/or in terms of the conformation of the first and/or of the second flow-directing surface, and/or in terms of the size and/or conformation of a flowthrough opening, constituted by the second flow-directing configuration and the distribution conduit, for a flow of therapeutic gas past the second flow-directing configuration.

With the nasal cannula therapy kit, using a single distribution conduit component and at least two plugs, preferably a plurality of plugs, it is possible to adapt the nasal cannula individually in terms of its flow conditions to the respective therapy instance by selecting from the plurality of available plugs a particular plug to be used. Because the plugs differ in the manner recited, for example by way of a different length of the plugs, the degree to which a branch opening is covered by the plug or by a flow-directing configuration can be modified. Additionally or alternatively, the deflection of the inflowing therapeutic gas to the branch opening associated with the respective flow-directing surface can be modified by selecting a plug with regard to a conformation of a flow-directing surface.

Additionally or alternatively, the proportion of therapeutic-gas flow that is directed to the two branch openings can also be modified by selecting a plug from a plurality of plugs having different flowthrough openings. One nasal cannula can thus be adapted in very simple fashion to a very large number of different therapeutic applications by selecting one plug from a plurality of plugs.

The present invention will be explained in further detail below with reference to the appended drawings, in which.

Figure 1:
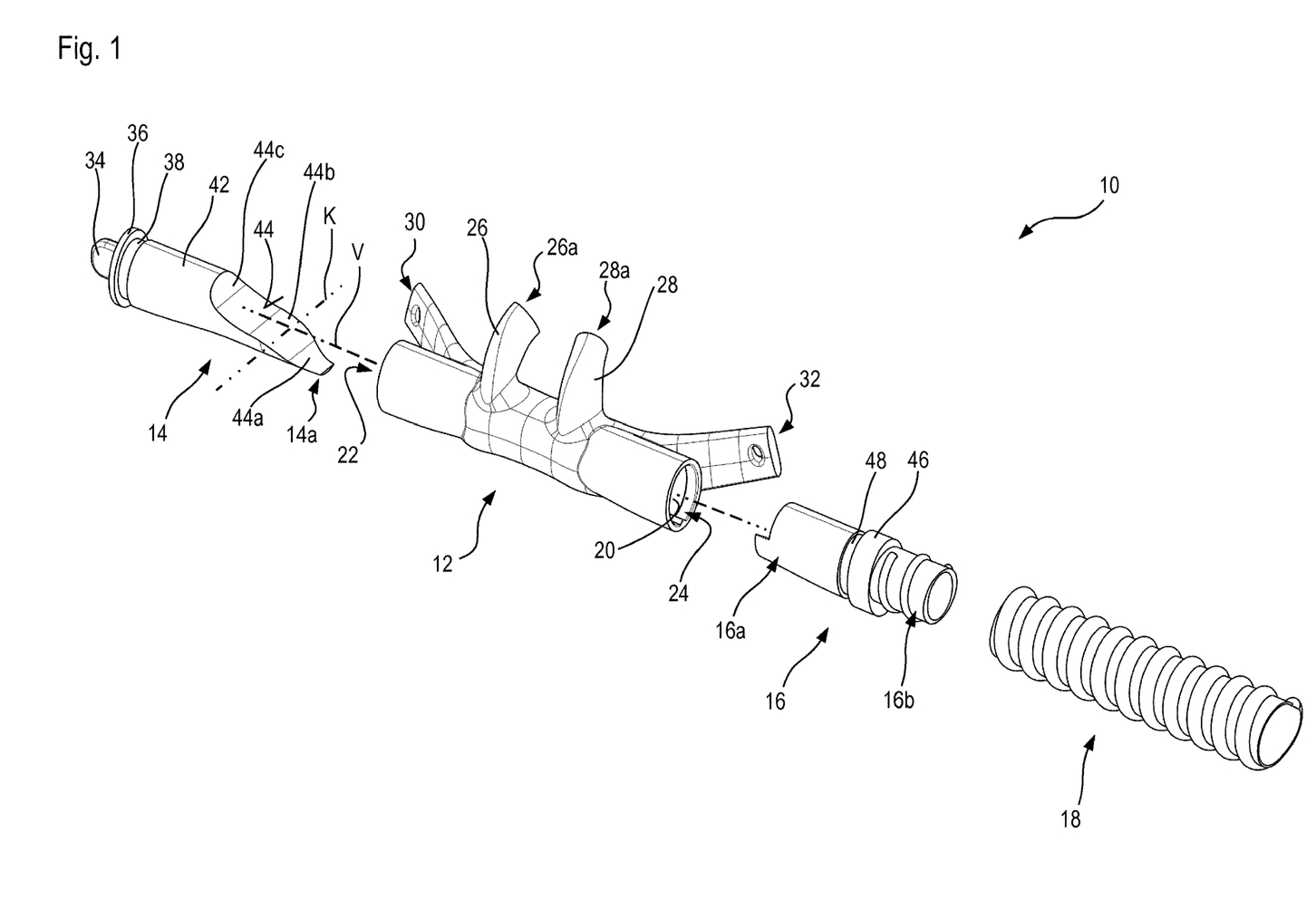
FIG. 1 is a schematic exploded view of a first embodiment of a nasal cannula according to the present invention.

In FIG. 1, a first embodiment of a nasal cannula according to the present invention is labeled in general with the number 10. Nasal cannula 10 encompasses a distribution conduit component 12, a plug 14, and a connector fitting 16. A delivery hose 18 can be attached, in particular threaded, onto the attachment portion 16*b* of connector fitting 16 which faces away from distribution conduit component 12 during operation.

Distribution conduit component 12 comprises a distribution conduit 20 extending along a distribution path V. Respective coupling openings 22 and 24, through which distribution conduit 20 is accessible, are embodied at axial longitudinal ends of distribution conduit component 12 which are opposite in terms of distribution path V. Branching off from distribution conduit component 12 are two supply conduits 26 and 28 that open into distribution conduit 20 of distribution conduit component 12. By means of support flanges 30 and 32, distribution conduit component 12 and thus nasal cannula 10 can be placed onto and worn by a patient in known fashion.

Distribution conduit component 12, including supply conduits 26 and 28 as well as support flanges 30 and 32, is preferably constituted in one piece, for instance by injection molding.

During therapeutic operation of nasal cannula 10, supply conduits 26 and 28 are brought, with their respective longitudinal ends 26*a* and 28*a* that are remote from distribution conduit 20, close to nostrils of a patient, or enter the patient's nasal cavities through the nostrils.

Figure 2:
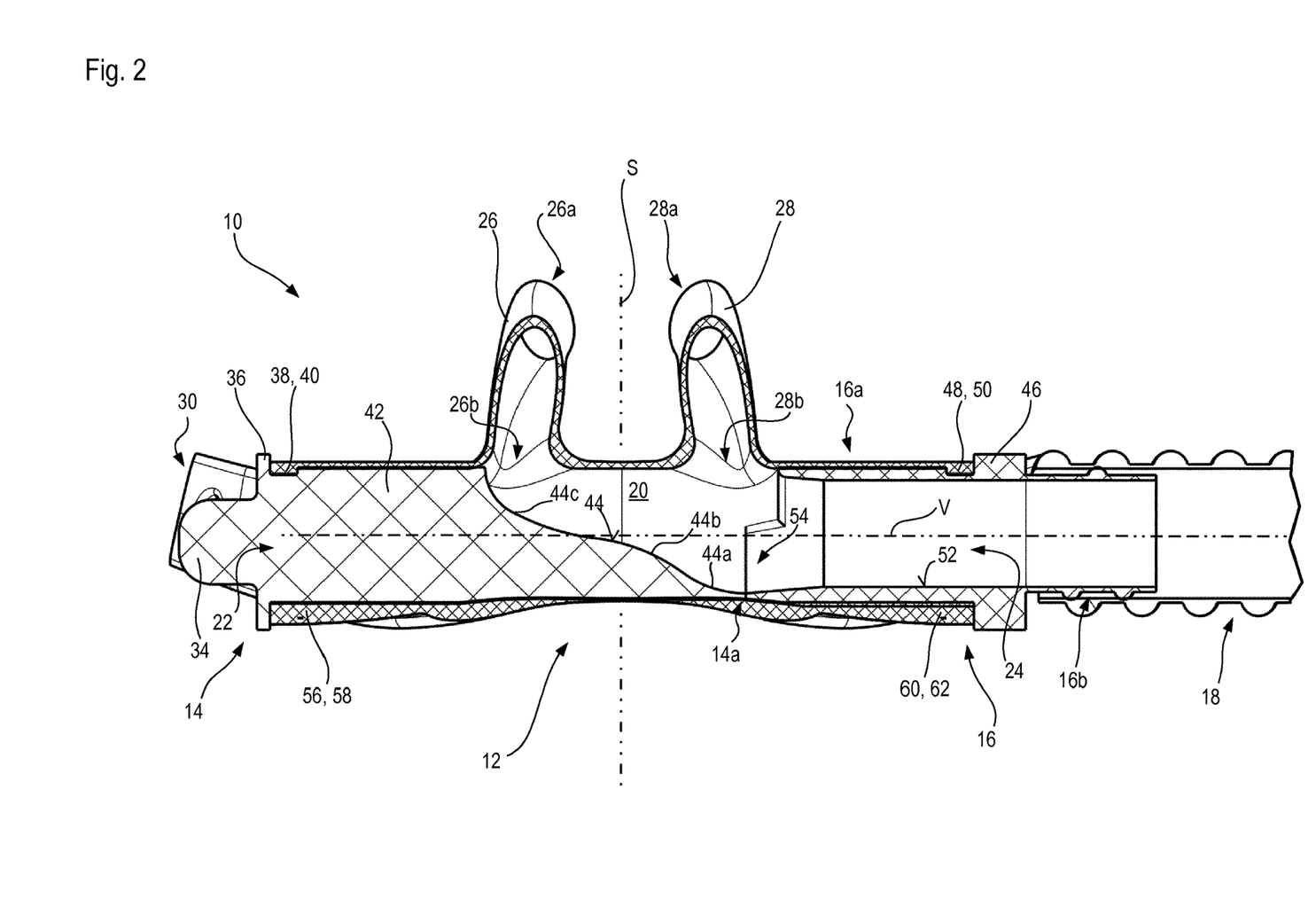
FIG. 2 is a schematic longitudinal section view through the embodiment of FIG. 1, the section plan containing the distribution path.

Distribution conduit component 12 is embodied mirror-symmetrically with respect to a symmetry plane S intersecting the rectilinear distribution path V orthogonally at half the distance between supply conduits 26 and 28 (see FIG. 2). This mirror-symmetrical embodiment has the advantage that coupling openings 22 and 24 are embodied identically, and thus that each is usable both by plug 14 and by connector fitting 16.

In the exploded view shown in FIG. 1, nasal cannula 10 is configured for gas delivery from the left side of a patient wearing nasal cannula 10. Coupling opening 24 is therefore a delivery opening 24.

Plug 14 is arranged and provided for placement through coupling opening 22 in distribution conduit 20 in order to avoid undesired emergence of therapeutic gas out of distribution conduit 20 through coupling opening 22. Coupling opening 22 therefore constitutes a closure opening 22.

Plug 14, preferably embodied in one piece and manufactured by injection molding, has at its one longitudinal end a grip attachment 34 that protrudes from a stop disk 36 which has a larger area than the inside cross-sectional area of coupling opening 22. Stop disk 36 thus projects beyond an edge of coupling opening 22 and thereby physically prevents excessive introduction of plug 14 into distribution conduit 20. When nasal cannula 10 is in the operationally ready state, stop disk 36 abuts against an edge of distribution conduit component 12 which delimits coupling opening 22, and thereby constitutes, with distribution conduit component 12, a mechanical stop.

Embodied on that side of stop disk 36 which is located oppositely from grip attachment 34 is a latching groove 38 into which, with nasal cannula 10 in the operationally ready state, a radial projection 40, extending around distribution path V, of distribution conduit component 12 engages in latching fashion (see FIG. 2). Radial projection 40 and latching groove 38 form a surmountable positive latching engagement that prevents undesired release of plug 14 from distribution conduit component 12, for instance as a result of the therapeutic-gas flow existing in distribution conduit 20.

A flow-directing configuration 42 adjoins latching groove 38 in a direction toward longitudinal introduction end 14*a* of plug 14. On its end facing away from grip attachment 34, flow-directing configuration 42 is delimited by a flow-directing surface 44 that, when plug 14 is introduced through coupling opening 22 into distribution conduit component 12 along distribution path V, constitutes a wall delimiting the flow space of distribution conduit 20. Therapeutic gas that emerges from connector fitting 16 in order to supply the patient with therapeutic gas flows onto flow-directing surface 44 during therapeutic operation.

In the present first exemplifying embodiment, flow-directing surface 44 is curved uniaxially, specifically exclusively around curvature axes that are arranged orthogonally to distribution path V. An exemplifying curvature axis K is indicated in FIG. 1. In the exemplifying embodiment depicted, flow-directing surface 44 is uncurved along curvature axis K, i.e. it exhibits rectilinear marginal lines in section planes orthogonal to distribution path V.

In the first exemplifying embodiment depicted in FIG. 1, flow-directing surface 44 has three regions having different types of curvature, namely a region 44*a* closest to longitudinal introduction end 14*a* and having a concave curvature, a region 44*b* adjacent thereto along distribution path V and having a convex curvature, and a third region 44*c* adjacent in turn to the latter region and having a concave curvature. Flow-directing surface 44 thus has two concave curvature regions 44*a* and 44*c* and one convex curvature portion 44*b* lying between them along distribution path V. The curvature of third curvature region 44*c* increases, i.e. its radius of curvature becomes smaller, with increasing proximity of concave curvature region 44*c* to supply conduit 26 (or 28, depending on the coupling opening 22 or 24 through which plug 14 is introduced into distribution conduit 20). This promotes low-loss and low-noise diversion of an initially axial therapeutic-gas flow flowing along distribution path V into supply conduit 26 that is associated with flow-directing surface 44 of plug 14 in the example depicted in FIG. 1.

So that it can be placed through each of the two coupling openings 22 and 24 with the same flow-directing effect in distribution conduit 20, plug 14 is symmetrical with reference to a symmetry plane that is oriented parallel to distribution path V and orthogonally to curvature axis K.

Connector fitting 16 is introducible with an introduction portion 16*a*, in the example shown in FIG. 1, through coupling opening 24 into distribution conduit 20 of distribution conduit component 12. Delivery hose 18 can be attached, in particular threaded, onto the oppositely located attachment portion 16*b*.

Connector fitting 16 comprises, between the introduction portion 16*a* and the attachment portion 16*b*, a stop ring 46 that projects radially beyond an edge of distribution conduit component 12 which delimits coupling opening 24, and thereby limits an introduction depth of connector fitting 16 into distribution conduit 20. Between introduction portion 16*a* and stop ring 46, connector fitting 16 also comprises a latching groove 48 into which a latching projection 50, extending around distribution path V, engages at that end region of distribution conduit component 12 which is located closer to coupling opening 24, in order to constitute a surmountable positive latching engagement when nasal cannula 10 is in the operationally ready state.

FIG. 2 depicts nasal cannula 10 of FIG. 1 in a longitudinal section view along a section plane containing distribution path V. Mirror symmetry plane S of distribution conduit component 12 is shown in FIG. 2; said plane is orthogonal to distribution path V and to the drawing plane of FIG. 2.

The section plane of the longitudinal section through nasal cannula 10 passes through the respective branch openings 26*b* and 28*b* from which supply conduits 26 and 28 extend away from distribution conduit 12. Branch openings 26*b* and 28*b* have the same cross-sectional area because of the aforementioned symmetry conditions, so that in principle a symmetrical supply of identical therapeutic-gas flow volumes through supply conduits 26 and 28 to both nostrils of a patient is possible. An inner surface 52 of connector fitting 16 forms, with flow-directing surface 44 of plug 14, one continuous flow-conveying surface 54. Inner surface 52 and flow-directing surface 44 transition flush into one another.

As is also evident from FIG. 2 and as has already been mentioned above in connection with FIG. 1, flow-directing surface 44 of plug 14 is uncurved in a direction orthogonal to the drawing plane of FIG. 2.

When plug 14 is seated correctly, concave portion 44*c* ends at the edge of branch opening 26*b* that is closest to plug 14 and is therefore associated therewith. Flow-directing surface 44, and in particular concave portion 44*c* thereof, are located in the longitudinal region of extent of branch opening 26*b*.

Flow-directing surface 44 in fact extends along distribution path V into the longitudinal direction of extent of branch opening 28*b*. Concave portion 44*b* of flow-directing surface 44 is therefore located for the most part, or in fact entirely, between branch openings 26*b* and 28*b* in a longitudinal direction along distribution path V.

As is apparent from FIG. 2, plug 14 and connector fitting 16 can easily exchange positions on distribution conduit component 12, which would result in a mirror-image supply of therapeutic gas through longitudinal ends 26a and 28a of supply conduits 26 and 28.

When a flow of therapeutic gas is flowing in from delivery opening 24, the configuration shown in FIG. 2 results in a very largely symmetrical flow of therapeutic gas through supply conduits 26 and 28, i.e. in a flow of approximately identical therapeutic-gas flow volumes through the two supply conduits 26 and 28.

Radial projection 40 on coupling opening 22 is not depicted in FIG. 2 as being completely encircling, since a radial projection 56—which constitutes a counterpart orientation configuration, extends along distribution path V, and protrudes radially inward toward distribution path V—is embodied on the underside of that wall of distribution conduit component 12 which delimits distribution conduit 20. This radial projection 56 engages into a complementary recess 58 constituting an orientation configuration in plug 14. In the arrangement situation depicted, both orientation configuration 58 in the form of the recess, and counterpart orientation configuration 56 in the form of the radial projection, taper in a radial direction toward distribution path V and in an axial direction from coupling opening 22 toward the longitudinal center of distribution conduit 20. This facilitates the introduction of plug 14 into the distribution conduit component from coupling opening 22 (or, because of the mirror-symmetrical embodiment of distribution conduit component 12 or at least of distribution conduit 20, also from coupling opening 24).

The positive engagement between orientation configuration 58 and counterpart orientation configuration 56 over a not inconsiderable axial length along distribution path V ensures that plug 14 is introducible into distribution conduit component 12 only in a defined relative orientation, so that flow-directing surface 44 is arranged correctly with respect to branch openings 26b and 28b.

Because of the mirror-symmetrical embodiment, distribution conduit component 12 also comprises, in the longitudinal end region of coupling opening 24, a counterpart arrangement configuration 60 in the form of a radial projection that engages into an arrangement configuration 62 of the connector fitting in the form of a recess. Once again, both recess 62 and radial projection 60 are embodied in such a way that they taper in a radial direction toward distribution conduit path V and taper in an axial direction from coupling opening 24 toward the longitudinal center of distribution conduit component 12. This ensures both correct arrangement of connector fitting 16 in distribution conduit component 11, and twist protection for said fitting around distribution path V relative to distribution conduit 20. Counterpart orientation configuration 56 and counterpart arrangement configuration 60 have in that regard an identical but opposite shape and have the same function or effect. The same is true of orientation configuration 58 on the one hand and arrangement configuration 62 on the other hand.

Distribution conduit component 12 is manufactured from a more flexible material than plug 14 and connector fitting 16. The material of distribution conduit component 12 thus has a lower modulus of elasticity than the materials of plug 14 and of connector fitting 16. This too facilitates the introduction of plug 14 and connector fitting 16 into distribution conduit component 12, and establishment of the positive latching engagement between latching projections 40 and 50 and the respective associated latching grooves 38 and 48, as well as establishment of the positive engagement between configurations 58 and 62 on the one hand and counterpart configurations 56 and 60 on the other hand.

Figure 3:
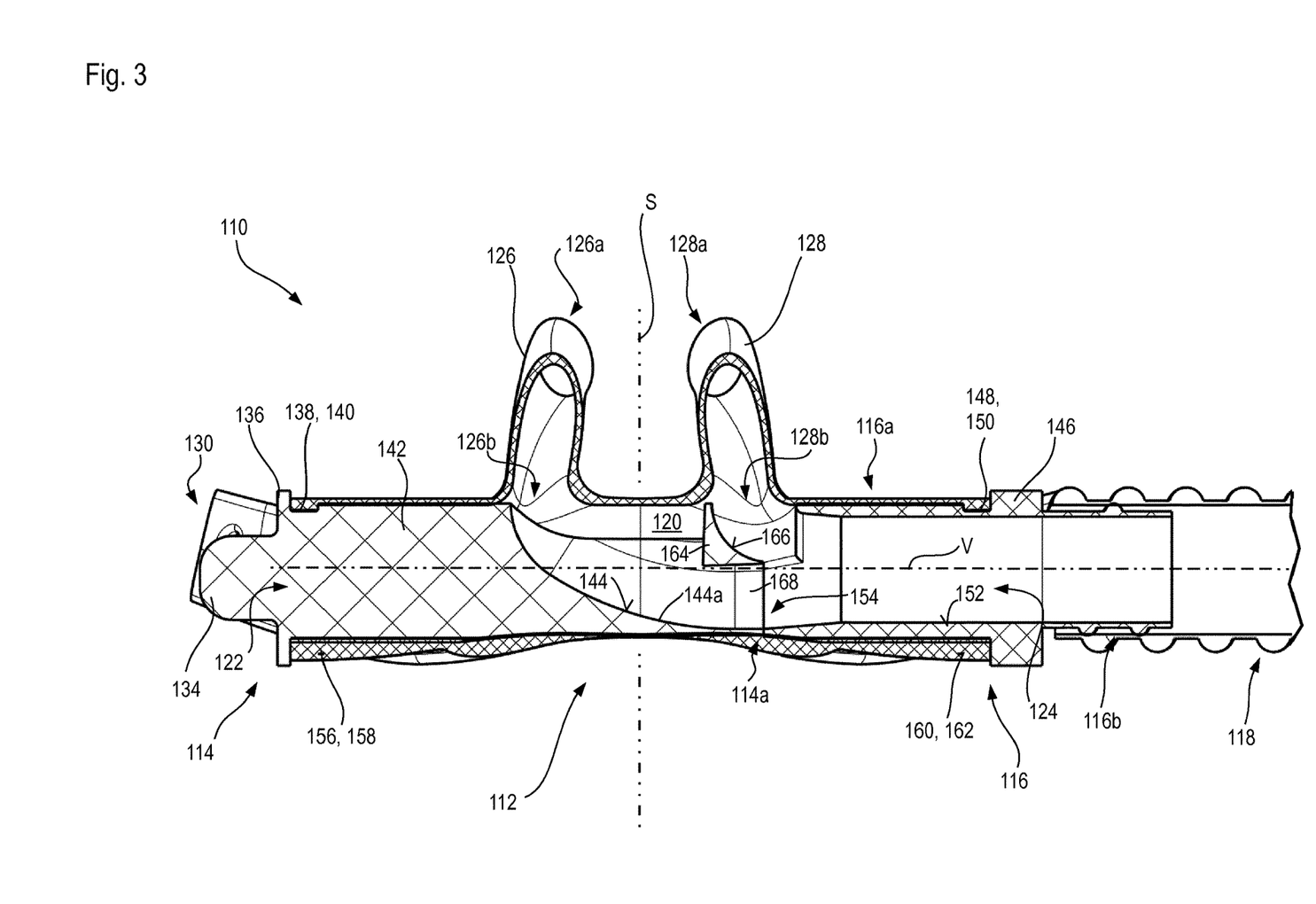
FIG. 3 is a longitudinal section view, corresponding to the view of FIG. 2, of a second embodiment of a nasal cannula according to the present invention having a plug differing from the nasal cannula of FIG. 2.

FIG. 3 depicts, along the same longitudinal section as nasal cannula 10 of FIG. 1, a second embodiment of a nasal cannula 110.

Components identical and functionally identical to those in the first embodiment of FIGS. 1 and 2 are labeled in the second embodiment of FIG. 3 with identical reference characters but incremented by 100.

The second embodiment of FIG. 3 will be explained below only insofar as it differs from the first embodiment of FIGS. 1 and 2, to the description of which reference is otherwise made for an explanation of the second embodiment of FIG. 3 as well.

Distribution conduit component 112, connector fitting 116, and delivery hose 118 are identical to the respective components 12, 16, and 18 of the first embodiment. Only plug 114 of the second embodiment of nasal cannula 110 differs from plug 14 of the first embodiment.

On the one hand, in the second embodiment flow-directing surface 144 is curved only concavely along distribution path V, i.e. comprises only a single concave surface portion 144a. The latter extends from longitudinal introduction end 114a of plug 114 to branch opening 126b associated with plug 114. It is, however, also the case for the single portion 144a curved concavely around a curvature axis orthogonal to distribution path V that the curvature increases, i.e. an associated radius of curvature becomes smaller, with increasing distance from longitudinal introduction end 114a and with increasing proximity to the associated branch opening 126b.

At the same time, flow-directing surface 144 is also concavely curved around a further curvature axis extending along distribution path V. Flow-directing surface 144 therefore forms a trough-shaped border around a flow space in the region of extent of plug 114.

A further salient difference between plug 114 and plug 14 is that there is embodied at the formers longitudinal introduction end 114a, separately from first flow-directing configuration 142, a second flow-directing configuration 164 having a second flow-directing surface 166 that is exposed to the therapeutic-gas flow flowing in from connector fitting 116 or from delivery opening 124, and is wettable thereby.

In contrast to first flow-directing surface 144 that is biaxially curved, second flow-directing surface 166 is curved only uniaxially, i.e. only around a curvature axis orthogonal to distribution path V. This need not be the case, however. Second flow-directing surface 166 as well can be curved both around a curvature axis orthogonal to distribution path V and around a curvature axis parallel to distribution path V. Second flow-directing surface 166 is located only in the longitudinal region of extent of branch opening 128b, and is therefore associated with the latter.

Second flow-directing configuration 164 extends over only approximately half the cross-sectional area of distribution conduit 120 at the point where second flow-directing configuration 164 is arranged, so that a flowthrough opening 168 remains between second flow-directing configuration 164 and that wall portion of distribution conduit 120 which lies diametrically oppositely from branch opening 128b that is associated with second flow-directing surface 166. Therapeutic gas flowing in from delivery opening 124 flows through this flowthrough opening 168 and past second flow-directing configuration 164, and reaches first flow-directing surface 144 and thus branch opening 126b associated with the latter. The cross-sectional area of flowthrough opening 168 corresponds approximately to half the cross-sectional area of distribution conduit 120 in the region where second flow-directing configuration 164 is arranged.

Thanks to second flow-directing configuration 164 with its second flow-directing surface 166, a portion of the therapeutic gas flowing in distribution conduit 120 can be deflected in controlled fashion into the one supply conduit 128, while first flow-directing surface 144 deflects the remaining portion of therapeutic gas into the respective other supply conduit 126.

Because flow-directing surfaces 144 and 166 are provided, therapeutic gas can be deflected in very largely loss-free fashion, with little noise, and in very controlled fashion to the individual branch openings 126b and 128b.

By means of differently configured plugs 14 and 114 that are introducible into one and the same respective distribution component 12 and 112, it is thereby possible to implement different therapeutic situations for the patient who is wearing nasal cannula 10 or 110, especially therapeutic situations in which therapeutic-gas flow volumes of different magnitudes flow in deliberate and controlled fashion through branch openings 126b and 128b and through supply conduits 126 and 128 adjoining them.

Figure 4:
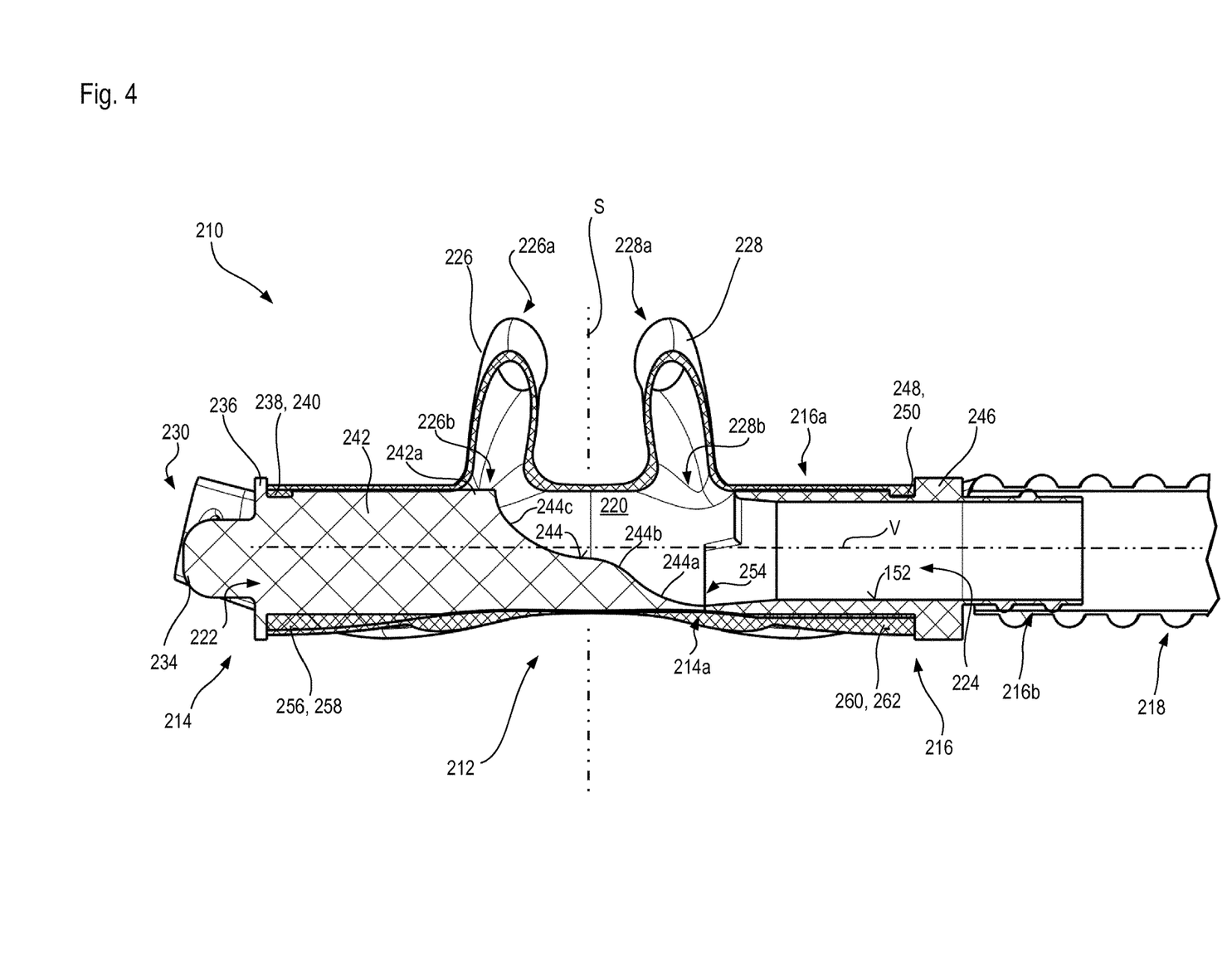
FIG. 4 is a further longitudinal section view, corresponding to the views of FIGS. 2 and 3, through a third embodiment according to the present invention of a nasal cannula having yet another differing plug.

FIG. 4 depicts a third embodiment in a longitudinal section corresponding to the view of FIGS. 2 and 3.

Components identical and functionally identical to those in the first embodiment are labeled in the third embodiment with identical reference characters but incremented by 200.

The third embodiment of FIG. 4 will be explained below only insofar as it differs from the first embodiment, to the description of which reference is otherwise made for an explanation of the third embodiment of FIG. 4 as well.

Once again, distribution conduit component 212, connector fitting 216, and delivery hose 218 are identical to the components of the same names of the first embodiment of FIGS. 1 and 2.

Plug 214 almost corresponds to plug 14 of the first embodiment. The single flow-directing surface 244 is curved only around curvature axes that extend orthogonally to distribution path V and orthogonally to the drawing plane of FIG. 4. Like the first embodiment, flow-directing surface 244 also comprises three differently curved curvature regions, namely a concave surface portion 244a located closest to longitudinal introduction end 214a, a convex surface portion 244b adjoining the latter portion along distribution path V, and a further concave surface portion 244c that adjoins the latter portion along distribution path V and extends as far as the associated branch opening 226b.

Flow-directing surface 244 of plug 214 of the third embodiment is, however, embodied to be shorter axially, i.e. along distribution path V, than flow-directing surface 44 of the first embodiment. Because the distance between longitudinal introduction end 214a and stop disk 236 of plug 214 is the same as in the first embodiment of plug 14, flow-directing configuration 242 forms a blocking portion 242a that partly closes off the associated branch opening 226b, so that branch opening 226b has a smaller effective flow cross section than the other branch opening 228b, which remains unclosed and uncovered.

With the third embodiment shown in FIG. 4, a different quantity of therapeutic gas per unit time can be intentionally directed through branch openings 226 and 228b of distribution conduit component 212, which are by design identical in size, so that therapeutic-gas flow volumes of different magnitudes can be administered in deliberate and controlled fashion to a patient via supply conduits 226 and 228.

It is of course also conceivable for plug 214, like plug 114, to additionally comprise a second flow-directing configuration.

Consideration can furthermore be given to generating therapeutic-gas flow volumes of different magnitudes through the branch openings by the fact that the flowthrough opening (see flowthrough opening 168 in FIG. 3) of the second flow-directing configuration is embodied to be smaller or larger than half the flow cross section of the distribution conduit.

These features—differently sized flowthrough opening and blocking portion 242a of flow-directing configuration 242—can also be used together on one and the same plug in order to generate therapeutic-gas flow volumes of different magnitudes in controlled fashion through branch openings 226b and 228b.

A projection or a recess can be embodied over a predetermined angular region at longitudinal introduction ends 14a, 114a, and 214a of plugs 14, 114, and 214, said projection projecting parallel to distribution path V, protrudingly from the longitudinal introduction end, into a recess on the leading longitudinal end of introduction portion 16a, 116a, 216a of connector fitting 16, 116, 216; or a corresponding projection at the leading longitudinal end of the connector fitting projecting into said recess that is indented parallel to distribution path V from the longitudinal introduction end, in order to secure the plug and the connector fitting not only respectively relative to the distribution conduit component, but also relative to one another, against twisting around distribution path V.

Figure 5:
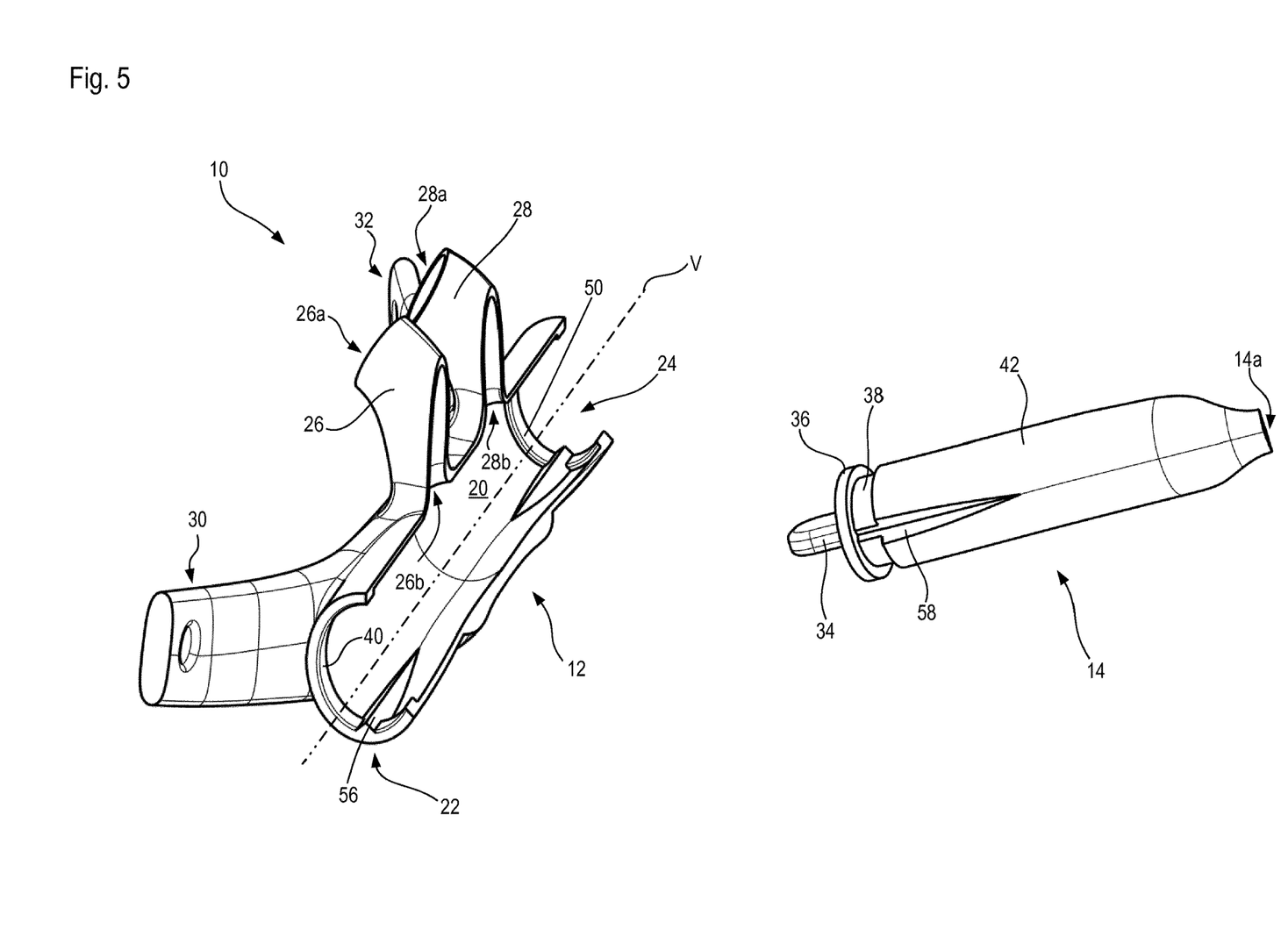
FIG. 5 is a partly sectioned perspective view of the distribution component, with a view from below of the plug of the first embodiment.

FIG. 5 shows distribution conduit component 12 in partial section. Counterpart orientation configuration 56 and counterpart arrangement configuration 60 in distribution conduit 20 are especially visible here. Plug 14 is also depicted here in a perspective view from below, so that orientation configuration 58 is shown here in its conformation that tapers both axially and radially. For reasons of symmetry, arrangement configuration 62 on the connector fitting has the same conformation.

One nasal cannula 10 can comprise different plugs 14, 114, and 214, so that a specific therapeutic situation can be created by selecting, from a plurality of available plugs, one plug that is used. A nasal cannula therapy kit that can be easily and quickly configured is thereby furnished for therapy-providing personnel.

The invention claimed is:

1. A nasal cannula for nasally supplying a patient with therapeutic gas, comprising a distribution conduit component having a distribution conduit that extends along a virtual distribution path passing centrally through it; the distribution path defining a longitudinal direction; the distribution conduit comprising two branch openings; a respective supply conduit for supplying the patient with the therapeutic gas from the distribution conduit branching off from each branch opening; the distribution conduit comprising, in addition to the branch openings, two coupling openings arranged at a distance from the branch openings; the nasal cannula further comprising a plug with which one of the two coupling openings, constituting a closure opening, is closable by the plug for a flow of gas through it; and a further one of the two coupling openings, constituting a delivery opening, being embodied for connection of a gas delivery line to the distribution conduit, wherein the plug comprises a flow-directing configuration having an exposed flow-directing surface; the flow-directing surface being arranged, in a reference state in which the plug is arranged on the nasal cannula so as to close off the closure opening, in the distribution conduit in a longitudinal region extending to at least one branch opening, and being canted with respect to the distribution path in such a way that it deflects the therapeutic gas, flowing in the distribution conduit in from the delivery opening along the distribution path, to at least one of the branch openings.

2. The nasal cannula according to claim 1, wherein the flow-directing surface has a concave curvature.

3. The nasal cannula according to claim 2, wherein the flow-directing surface is concavely and/or convexly curved at least locally around a curvature axis orthogonal to the distribution path.

4. The nasal cannula according to claim 3, wherein the flow-directing surface is also concavely curved around a curvature axis extending along the distribution path.

5. The nasal cannula according to claim 1, wherein the nasal cannula comprises a connector fitting that is introducible into the delivery opening for connection of the gas delivery line, an inner surface of the connector fitting which directs the gas flow through the connector fitting, when arranged in an operationally ready state on the nasal cannula, forming a continuous flow-conveying surface with the flow-directing surface.

6. The nasal cannula according to claim 5, wherein the plug comprises a positive-engagement configuration; and the connector fitting comprises a counterpart positive-engagement configuration, the positive-engagement configuration and the counterpart positive-engagement configuration being in positive engagement with one another in the operationally ready state.

7. The nasal cannula according to claim 5, wherein the connector fitting comprises an arrangement configuration; and the distribution conduit component comprises a counterpart arrangement configuration in the region of the delivery opening, the arrangement configuration and the counterpart arrangement configuration being in positive engagement with one another in the operationally ready state, of the nasal cannula.

8. The nasal cannula according to claim 1, wherein the plug comprises an orientation configuration; and the distribution conduit component comprises a counterpart orientation configuration in the region of the closure opening; the orientation configuration and the counterpart orientation configuration being in positive engagement with one another in the operationally ready state, of the nasal cannula.

9. The nasal cannula according to claim 1, wherein the two coupling openings are embodied similarly to the extent that each of the two coupling openings can be both a closure opening and a delivery opening.

10. The nasal cannula according to claim 1, wherein the plug, in the reference state, at least partly closes off the branch opening located closer to the closure opening.

11. The nasal cannula according to claim 1, wherein the flow-directing surface is a first flow-directing surface and the flow-directing configuration is a first flow-directing configuration that deflects the therapeutic gas, flowing in from the delivery opening along the distribution path, to one of the branch openings; the plug having a second flow-directing configuration having a second flow-directing surface that is arranged at a distance along the distribution path from the first flow-directing configuration and that, in the reference state, deflects the therapeutic gas, flowing in from the delivery opening along the distribution path, to the respective other branch opening.

12. The nasal cannula according to claim 11, wherein the second flow-directing configuration extends over only a partial cross-section of the distribution conduit and, where the second flow-directing configuration extends it deflects the therapeutic gas flowing in along the distribution path into the respective other branch opening, and outside where the second flow-directing configuration extends it constitutes, together with the distribution conduit, a flow-through opening for a flow of the therapeutic gas past the second flow-directing configuration to the first flow-directing surface, through which a portion of the therapeutic gas flowing in from the delivery opening can flow to the first flow-directing configuration.

13. The nasal cannula according to claim 11, wherein the second flow-directing configuration abuts against an inner wall of the distribution conduit over a predetermined angular region around the distribution path which is constituted from several angular sub-regions located at a distance from one another.

14. The nasal cannula according to claim 12 or, wherein a cross-sectional area, flow-through-capable for the therapeutic gas, of the flow-through opening is larger or smaller than half the cross-sectional area of the distribution conduit at the location of the flow-through opening.

15. The nasal cannula according to claim 1, wherein the distribution conduit component is constituted from a material that has a lower modulus of elasticity than the material of the plug and/or of a connector fitting, so that the distribution conduit component is deformable by the respective insertion component upon introduction of one insertion component from among the plug and/or connector fitting into the distribution conduit component.

16. The nasal cannula according to claim 1, wherein the two coupling openings are located at opposite longitudinal ends of the distribution conduit.

17. The nasal cannula according to claim 16, wherein the distribution path extends in a straight line between the two coupling openings.

18. A nasal cannula therapy kit comprising:
a nasal cannula for nasally supplying a patient with therapeutic gas comprising a distribution conduit component having a distribution conduit that extends along a virtual distribution path passing centrally through it; the distribution path defining a longitudinal direction; the distribution conduit comprising two branch openings; a respective supply conduit for supplying the patient with the therapeutic gas from the distribution conduit branching off from each branch opening; the distribution conduit comprising, in addition to the branch openings, two coupling openings arranged at a distance from the branch openings; and
at least two plugs, wherein a closure opening of the two coupling openings is closable by one of the at least two plugs for a flow of gas through it; and a delivery opening of the two coupling openings being embodied for connection of a gas delivery line to the distribution conduit,
wherein each of a first plug and a second plug of the at least two plugs comprises a first flow-directing configuration having a first flow-directing surface; the first flow-directing surface being arranged, in a reference state in which either the first plug or the second plug is arranged on the nasal cannula so as to close off the closure opening, in the distribution conduit in a longitudinal region extending to at least one branch opening, and being canted with respect to the distribution path in such a way that it deflects the therapeutic gas, flowing in the distribution conduit in from the delivery opening along the distribution path, to at least one of the branch openings, wherein a second plug of the at least two plugs comprises a second flow-directing configuration having a second flow-directing surface that is arranged at a distance along the distribution path from the first flow-directing configuration and that, in the reference state in which the second plug is arranged on the nasal cannula so as to close off the closure opening, the second flow-directing surface deflects the therapeutic gas, flowing in from the delivery opening along the distribution path, to the respective other branch opening, wherein the first flow-directing configuration and the second flow-directing configuration differ in length, and/or wherein the first flow-directing surface and the second flow-directing surface differ in conformation; and/or the second flow-directing configuration extends over only a partial cross-section of the distribution conduit and, where the second flow-directing configuration extends it deflects the therapeutic gas flowing in along the distribution path into the respective other branch opening, and outside where the second flow-directing configuration extends, it constitutes, together with the distribution conduit, a flow-through opening for a flow of the therapeutic gas past the second flow-directing configuration to the first flow-directing surface, through which a portion of the therapeutic gas flowing in from the delivery opening can flow to the first flow-directing configuration.

* * * * *

UNITED STATES PATENT AND TRADEMARK OFFICE
CERTIFICATE OF CORRECTION

| | |
|---|---|
| PATENT NO. | : 11,666,723 B2 |
| APPLICATION NO. | : 17/273495 |
| DATED | : June 6, 2023 |
| INVENTOR(S) | : Schwaiger et al. |

It is certified that error appears in the above-identified patent and that said Letters Patent is hereby corrected as shown below:

In the Claims

In Claim 1, Column 17, Line 3, insert -- of the -- between "one" and "branch" and -- opening -- should read -- openings --

In Claim 18, Column 18, Line 65, insert -- of the -- between "one" and "branch" and -- opening -- should read -- openings --

Signed and Sealed this
Twenty-sixth Day of December, 2023

Katherine Kelly Vidal
*Director of the United States Patent and Trademark Office*